(12) United States Patent
Munsif (10) Patent No.: US 11,119,088 B2
(45) Date of Patent: Sep. 14, 2021

(54) SYSTEM AND METHOD FOR CALCULATING THE RESEARCH OCTANE NUMBER AND THE MOTOR OCTANE NUMBER FOR A LIQUID BLENDED FUEL

(71) Applicant: Chevron U.S.A. Inc., San Ramon, CA (US)

(72) Inventor: Himal Pravin Munsif, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 7 days.

(21) Appl. No.: 16/816,866

(22) Filed: Mar. 12, 2020

(65) Prior Publication Data

US 2020/0292518 A1    Sep. 17, 2020

Related U.S. Application Data

(60) Provisional application No. 62/819,291, filed on Mar. 15, 2019.

(51) Int. Cl.
| | | |
|---|---|---|
| *G01N 33/28* | (2006.01) | |
| *G01N 33/22* | (2006.01) | |
| *C01B 3/00* | (2006.01) | |
| *G01N 30/78* | (2006.01) | |

(52) U.S. Cl.
CPC ......... *G01N 33/2829* (2013.01); *G01N 33/22* (2013.01); *C01B 3/0015* (2013.01); *G01N 30/78* (2013.01)

(58) Field of Classification Search
CPC .. C01B 3/0015; G01N 33/2829; G01N 33/22; G01N 30/78
See application file for complete search history.

(56) References Cited

U.S. PATENT DOCUMENTS 4,904,604 A * 2/1990 Kivlen ............... G01N 33/2823
436/139
4,963,745 A * 10/1990 Maggard .............. G01N 21/359
250/343

(Continued)

FOREIGN PATENT DOCUMENTS

EP       0285251 A1    10/1988

OTHER PUBLICATIONS

Rusin, M. H., "A "Transformation" Method for Calculating the Research and Motor Octane Numbers of Gasoline Blends", Ind. Eng. Chem. Fundam. v 20, pp. 195-204 (1981).

*Primary Examiner* — David A. Rogers
(74) *Attorney, Agent, or Firm* — E Joseph Gess; Melissa M. Hayworth; Terrence M. Flaherty (57) ABSTRACT

A method for calculating the research octane number and the motor octane number for a liquid blended fuel. Data related to the aromatic, olefin, normal paraffin, iso-paraffin, and naphthalene properties of each of a plurality of liquid fuel blending components are acquired and transformed to obtain a transformed component property for each of the components. A reverse property transformation is performed for each of the plurality of liquid blending components. The research octane number and the motor octane number are calculated based on the performed reverse property transformation and determined percentages of each of the plurality of liquid blending components.

13 Claims, 5 Drawing Sheets

(56) References Cited

U.S. PATENT DOCUMENTS

| | | | | |
|---|---|---|---|---|
| 5,121,337 A * | 6/1992 | Brown | | G01N 21/274 |
| | | | | 250/339.12 |
| 5,223,714 A | 6/1993 | Maggard | | |
| 5,349,188 A | 9/1994 | Maggard | | |
| 5,641,962 A | 6/1997 | Perry et al. | | |
| 5,653,866 A * | 8/1997 | Jessup | | C10L 1/06 |
| | | | | 123/1 A |
| 5,699,269 A * | 12/1997 | Ashe | | G01N 33/2823 |
| | | | | 702/30 |
| 5,796,251 A * | 8/1998 | Le Febre | | G01N 33/2829 |
| | | | | 324/300 |
| 5,851,241 A * | 12/1998 | Studzinski | | C10L 10/10 |
| | | | | 44/359 |
| 5,892,228 A | 4/1999 | Cooper et al. | | |
| 6,609,413 B1 * | 8/2003 | De Craecker | | G01N 33/2829 |
| | | | | 73/35.02 |
| 8,645,079 B2 * | 2/2014 | Albahri | | G16C 20/30 |
| | | | | 702/22 |
| 9,201,053 B2 * | 12/2015 | Albahri | | G16C 20/30 |
| 9,709,545 B2 * | 7/2017 | Mertens | | G01N 33/22 |
| 9,862,905 B2 * | 1/2018 | Prakash | | C10L 1/232 |
| 10,228,708 B2 * | 3/2019 | Lambert | | G01N 33/22 |
| 10,288,588 B2 * | 5/2019 | Morris | | G01N 33/2829 |
| 2009/0282897 A1 * | 11/2009 | Bertoncini | | G01N 33/2811 |
| | | | | 73/23.38 |
| 2014/0075831 A1 * | 3/2014 | Kelly | | C10L 1/023 |
| | | | | 44/451 |
| 2014/0229010 A1 * | 8/2014 | Farquharson | | G01N 33/22 |
| | | | | 700/272 |
| 2015/0112611 A1 * | 4/2015 | Koseoglu | | G01N 33/2823 |
| | | | | 702/25 |
| 2015/0159100 A1 * | 6/2015 | Shi | | C10L 1/04 |
| | | | | 585/14 |
| 2016/0091467 A1 * | 3/2016 | Morris | | G01N 30/8675 |
| | | | | 73/23.37 |
| 2017/0269018 A1 * | 9/2017 | Brown | | G01K 7/16 |
| 2020/0209213 A1 | 7/2020 | Koseoglu | | G01N 33/2829 |

* cited by examiner

SYSTEM AND METHOD FOR CALCULATING THE RESEARCH OCTANE NUMBER AND THE MOTOR OCTANE NUMBER FOR A LIQUID BLENDED FUEL

RELATED APPLICATIONS

This application claims priority to U.S. Provisional Application No. 62/819,291, filed Marc. 15, 2019, which application is incorporated herein by reference in its entirety.

FIELD OF ART

The present disclosure relates to methods and systems for calculating the research octane number ("RON") and the motor octane number ("MON") for a liquid blended fuel. More specifically, the present disclosure relates to methods for calculating the RON and the MON for a liquid blended fuel based on transformations of data related to at least the aromatic, olefin, normal paraffin, iso-paraffin, and naphthene properties of each of a plurality of liquid blending components.

BACKGROUND OF THE INVENTION

Liquid fuels, such as gasoline, can be manufactured by blending a plurality of components together to form a final product for fueling various motors and machinery. The actual composition of the gasoline, including its various components and additives, varies by location and producer. Nevertheless, each batch of blended fuel must be within certain tolerances to comply with contracts and regulations. Refineries blend various gasoline blendstocks to produce finished gasoline fuel that meets product requirements. One such requirement is octane number, which reflects the gasoline's antiknock quality. For example, targeted blended fuels must be within tolerances to sell as having an octane number of 87 or having an octane number of 93. Octane numbers blends nonlinearly, and traditionally gasoline manufacturers have used correlations (index or nonlinear) to predict or calculate blended octane numbers.

Two of the properties by which the composition of a liquid blended fuel is measured are research octane number ("RON") and motor octane number ("MON"). The RON describes the behavior of the fuel in an engine at lower operating temperatures and speeds, and represents an attempt to simulate acceleration behavior. The MON describes the behavior of the fuel in an engine at high operating temperatures and speeds, such as at fuel-throttle, not merely as driving fast on a highway. Not to be confused with the RON, the Road Octane Number for a blended fuel is the average between the RON and MON. In other words, the Road Octane Number is calculated by summing the RON and the MON, and dividing by two.

Similar to octane, the liquid blended fuel must be within certain tolerances of a targeted Road Octane Number as measured at the fuel pump. In the past, fuel manufacturers have been able to produce blended fuels having Road Octane Numbers within acceptable tolerances. However, the individual components of the Road Octane Numbers, the RON and the MON of the fuels, may have been far off targeted levels. The RON value is often too high, and the MON is often too low. For example, a blended fuel targeted to have an 87 octane blend typically has a RON of 91-93 and a MON of 82-84. Fortunately, the RON and MON of the blends tend to cancel each other out when blended and distributed at the fuel pump, thereby resulting in a Road Octane Number that is within targeted tolerances. Even so, the errors from the targeted values of the RON and the MON are problematic because they negatively affect engine performance, such as at low and high speeds. Further, various gasoline products have targeted RON and MON values which are not consistently met even though the Road Octane Number value is within tolerances. These deviations cause supply delays (waiting for replacement shipments that are within RON and MON tolerances) and excess production costs (from excess RON production and inefficient use of energy), both of which cause significant cost to the manufacturer of the blended fuel. For example, it is more expensive to produce a blended fuel having a RON of 91-93 than to produce a blended fuel closer to a targeted 87 value.

Due to the inaccuracy of predicting the RON and MON values of individual fuel streams, there is a risk of misrepresenting the unit operations in linear program production and blending models and associated octane control mechanisms. This can lead to inefficient operating plans (by targeting suboptimal reformer octanes) and misrepresents the economics of capital projects resulting from the over-prediction of RON, for example. Further, the trial-and-error and biasing techniques used to attempt to achieve optimal percentages of fuel component blends is expensive and time-consuming. Therefore, there is a need for a method for predicting with greater accuracy RON and MON values.

SUMMARY OF THE INVENTION

In a first aspect, a method for calculating the research octane number and the motor octane number for a liquid blended fuel is disclosed. The method includes acquiring data related to the aromatic, olefin, normal paraffin, iso-paraffin, and naphthene properties of each of a plurality of liquid blending components, wherein the plurality of liquid blending components are configured to be combined to produce a liquid blended fuel product. It is important that the properties of normal paraffin, iso-paraffin, and naphthene are accounted for individually, as is their interaction. The method provides for transforming the acquired data for each of the liquid blending components to obtain a transformed component property value for each of the plurality of liquid blending components; and linearly blending the transformed component properties for each of the plurality of blending components to obtain a transformed blended property for the plurality of liquid blending components. The method proceeds by performing reverse property transformation on the transformed blended property value for each of the plurality of liquid blending components; determining the percentages of each of the plurality of liquid blending components for combining to produce the liquid blended fuel product; calculating the research octane number of the blended fuel product; and calculating the motor octane number of the blended fuel product.

In a second aspect, a system for calculating the research octane number and the motor octane number for a liquid blended fuel is disclosed. The system includes a processing device; and a computer readable storage device storing computer readable instructions that, when executed by the processing device, cause a computing device to acquire data related to the aromatic, olefin, normal paraffin, iso-paraffin, and naphthene properties of each of a plurality of liquid blending components; transform the acquired data for each of the liquid blending components to obtain a transformed component property value for each of the plurality of liquid blending components; and linearly blend the transformed component property value for each of the plurality of liquid blending components to obtain a transformed blended property value for the each of the plurality liquid blending components. The instructions, when executed by the processing device, further cause the computing device to perform reverse property transformation on the transformed blended property value for each of the plurality of liquid blending components; determine the percentages of each of the plurality of liquid blending components for combining to produce a liquid blended fuel product; calculate the research octane number of the blended fuel product; and calculate the motor octane number of the blended fuel product.

In a third aspect, a method for blending a plurality of liquid blending components to produce a liquid petroleum fuel with a targeted research octane number and a targeted motor octane number is disclosed. The method includes determining a targeted research octane number and a tolerance range for the research octane number; determining a targeted motor octane number and a tolerance range for the motor octane number; acquiring data related to the aromatic, olefin, normal paraffin, iso-paraffin, and naphthene properties of each of a plurality of liquid blending components; transforming the acquired data for each of the liquid blending components to obtain a transformed component property value for each of the liquid blending components; linearly blending the transformed component property value for each of the liquid blending components to obtain a transformed blended property value for each of the plurality of liquid blending components; and performing reverse property transformation on the transformed blended property value for each of the plurality of liquid blending components. The method further includes determining the percentage of each of the plurality of liquid blending components which, when blended together according to the determined proportions, produce a blended fuel product comprising the determined targeted research octane number within the tolerance range for the research octane number and comprising the determined targeted motor octane number within the tolerance range for the motor octane number; and utilizing the determined proportion of each of the liquid blending components to tune a linear program model configured to produce the blended fuel product.

BRIEF DESCRIPTION OF THE DRAWINGS

The accompanying drawings, which are incorporated in and constitute a part of this disclosure, illustrate various aspects. In these drawings, like reference numbers have been used to designate like elements, and.

DETAILED DESCRIPTION OF THE INVENTION

As briefly discussed above, embodiments of the present invention are directed to systems and methods for calculating the research octane number and the motor octane number for a liquid blended fuel. Gasolines are well known fuels that fall into the category of liquid blended fuels that are included within embodiments of this application. Gasolines are generally composed of a mixture or blend of various hydrocarbons having different properties, including differing proportions of aromatics, olefins, normal paraffins, iso-paraffins, and naphthenes.

Government regulations, environmental concerns, and demands to reduce fuel costs have motivated engine companies and fuel manufacturers to develop and refine their respective products to produce engines and fuels that meet existing and anticipated regulations and that work well together in so doing. Producing fuels that effectively and efficiently meet these requirements is a complex process given the multiple components that are mixed and blended to produce an output liquid blended fuel and given the multiple sources and therefore composition for the individual fuel components.

The methods and systems of this invention integrate the acquisition, transformation, and blending of the properties of each of a plurality of component fuels into a practical application for efficiently and cost-effectively blending the component fuels together in particular percentages to produce a liquid blended fuel having predetermined properties. By providing methods for calculating RON and MON values for a liquid blended fuel, the present invention provides benefits over contemporary methods and systems for blending fuels by more accurately calculating and blending fuels having targeted RON and MON values, thereby reducing costs, reducing redelivery occurrences and times, and delivering liquid blended fuels with a composition more closely suited to targeted usages. For export grades of blended fuel, the disclosed methods provide more optimal recipes and reduces finished octane giveaway, which lowers the cost-to-produce. Improvements to the linear program model for predictions and calculations will result in better targeting optimal reformer octanes and octane control mechanisms while also avoiding erroneous forecast economies while evaluating capital projects in refineries.

Each of the components that comprise a liquid blended fuel include aromatics, olefins, normal paraffins, iso-paraffins, and naphthenes, which all have particular properties and qualities. Under contemporary blending practices, the paraffin, iso-paraffin, and naphthene qualities are lumped together under a saturates category (alternately referred to as paraffins). This grouping has been done for decades because it has been an accepted faster and cheaper technique to produce a blended fuel with a road octane number within tolerances. Also, only data on the aromatic, olefin, and saturates qualities has been available under the standard fluorescence indicator adsorption (FIA) technique for property analysis. Accordingly, the property data associated with the paraffin, iso-paraffin, and the grouped saturates for each of the component liquids to be blended into the output liquid blended fuel have been and are utilized to estimate the RON and the MON of the blended fuel. However, this grouping of normal paraffin, iso-paraffin, and naphthene values into a single saturates value has been found to result in a loss of any property details associated with the particular normal paraffin, iso-paraffin, and naphthene properties within each fuel component, thereby compromising the accuracy of the RON and MON values for the resulting blended fuel. Further, the normal paraffins and iso-paraffins tend to interact with the naphthenes in the component fuels, further hindering any measurement or calculation of the properties of the resulting liquid blended fuel. The saturates breakup of normal paraffins, iso-paraffins and naphthenes can now be differentiated using gas chromatography (GC) techniques or detailed hydrocarbon analysis (DHA) according to ASTM D6729. Departure from linear blending produced by the iso-paraffin/aromatic interaction is opposite to the departure produced by the iso-paraffin/naphthene interaction. These effects cannot be modeled using only FIA analyses. Characterizing the oil with naphthenes, iso-paraffins, and normal paraffins provides a more complete picture of molecule class octane interaction than does saturates alone. This is the heart of the idea presented here and described in equations 2c and 2d below. Accordingly, the prior existing calculations of RON and MON values are inherently imprecise given the lack of individual property data related to the normal paraffin, iso-paraffin, and naphthene properties. By accounting for the specific properties and qualities of normal paraffins, iso-paraffins, and naphthenes, instead of lumping them together, a greater accuracy in predicting RON and MON is possible.

Figure 1:
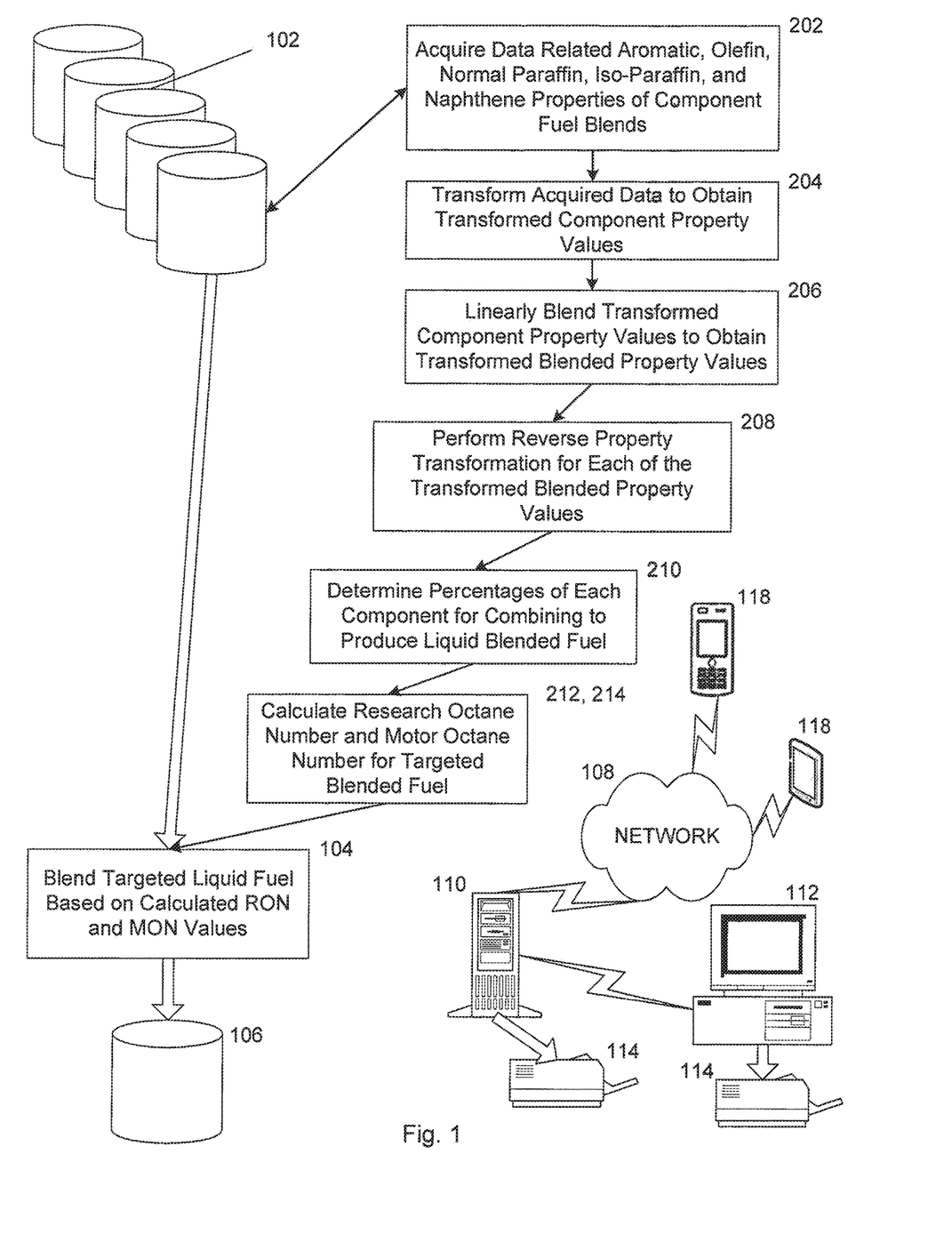
FIG. 1 schematically depicts an exemplary operating environment for calculating the research octane number and the motor octane number values for a liquid blended fuel and for blending component petroleum liquids into the liquid blended fuel product.

Referring to FIG. 1, there is shown an exemplary operating environment for calculating the research octane number and the motor octane number values for a liquid blended fuel and for blending component petroleum liquids into the liquid blended fuel product 106. Tanks holding possible liquid components for being combined into an output liquid blended fuel product are shown at 102. While an exemplary number of tanks 102 and 106 are shown, any number of tanks, typically one tank per fuel component, can be used. Also, while not shown, fuel components can also be provided through pipelines, tanker trucks, and other delivery devices; any number or combination of which can be utilized within the processes and components of these disclosed methods and systems. Element number 102 and 106 are used interchangeably herein to refer to both the physical container and the product contained therein.

The methods and systems disclosed herein are intended to be controlled by computer, such as the computers shown as 110 and 112, and also as mobile devices 118, with control, monitoring, and communications optionally being effected over one or more networks 108. The computers can collectively or individually be considered a computing device. Each of these computers comprise one or more computer readable storage devices for the storage of at least data and computer readable instructions. The instructions are retained in a non-volatile memory or storage area. Each computer also has one or more processing devices for the processing of instructions, the analysis of data, and the management of communications. Output reports can be generated for printing on exemplary output devices 114 and for display on computers 110 and 112 and on mobile devices 118. Control inputs from users can be provided through any and all of computers 110 and 112 and mobile devices 118, subject to authentication and authorization controls. The instructions can be combined in software, modules, and programs to control the hardware, equipment, and processes disclosed herein for calculating various properties of component fuels and output blended fuel products. For example, the instructions can be assembled in a linear program module, including connected and controlled equipment, for producing a blended fuel product.

Figure 2:
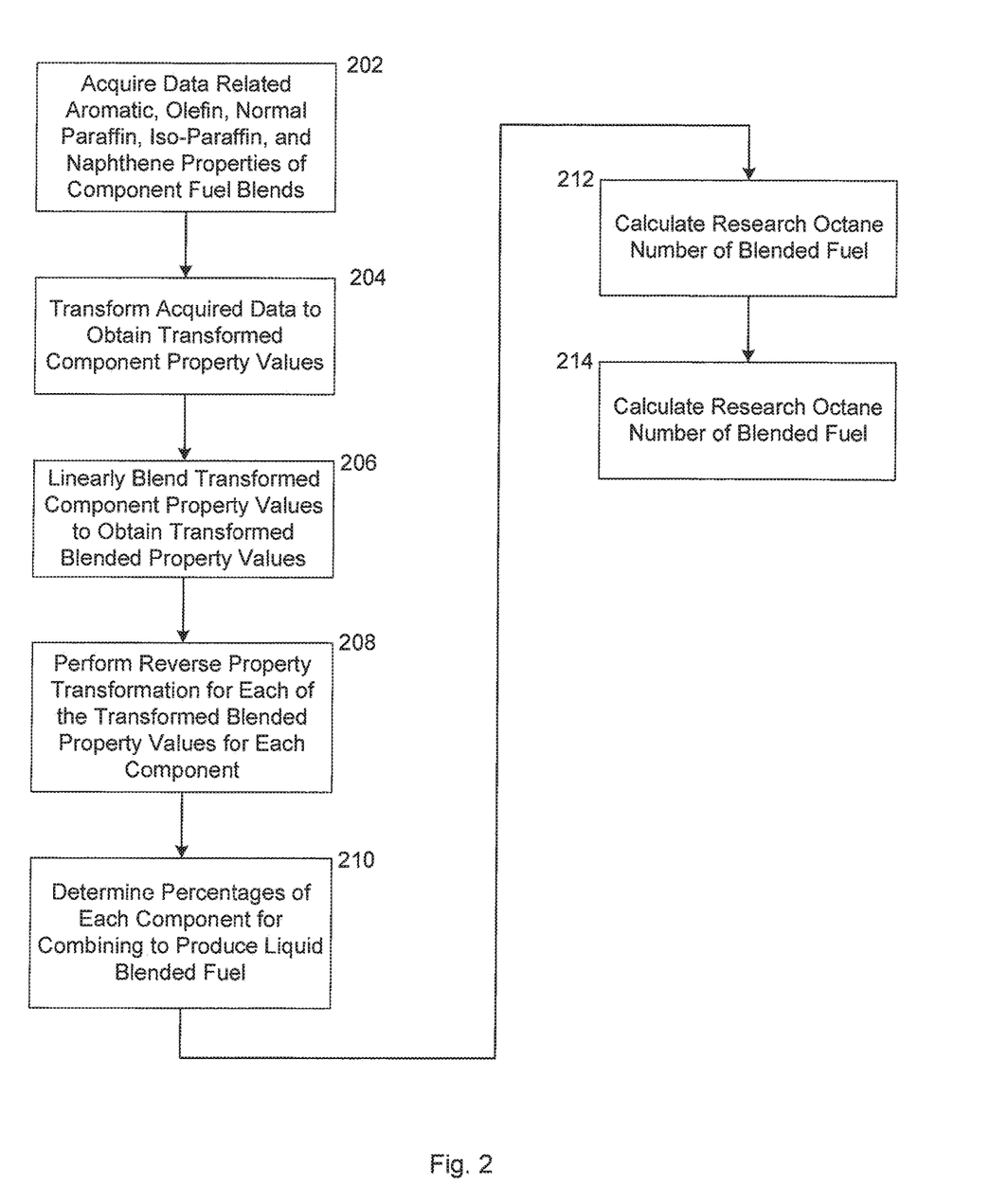
FIG. 2 illustrates a flowchart of a method for calculating the research octane number and the motor octane number for a liquid blended fuel, according to an example embodiment of the invention.
Figure 3:
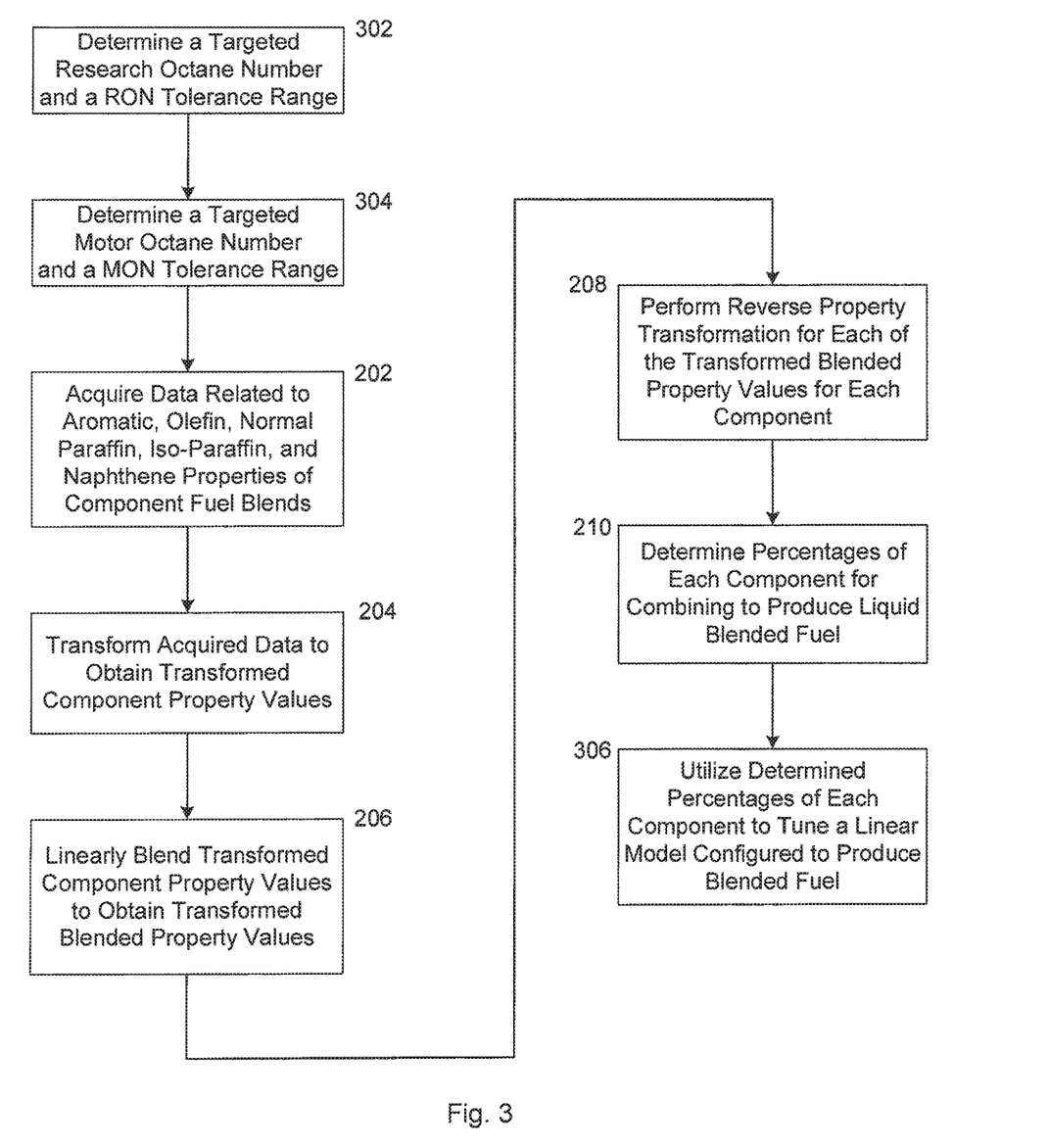
FIG. 3 illustrates a flowchart of a method for blending a plurality of liquid blending components to produce a liquid petroleum fuel with a targeted research octane number and a targeted motor octane number.

The methods and systems disclosed herein are computer controlled to provide for reliable, predictable, and controllable processes for the automatic calculation of RON and MON values; for the automated reception and analysis of multiple data types; and for the automated blending of a plurality of liquid blending components 102 into an output liquid blended fuel product 106. While not shown in FIG. 1, sensors and other measuring devices are located throughout the system for the recording of properties associated with the liquid blending components 102 and the output liquid blended fuel product 106. For example, values for the aromatic, olefin, normal paraffin, iso-paraffin, and naphthene properties of the liquid blending components 102 can be acquired for input to the disclosed systems and processes. Further, properties such as the research octane number and the motor octane number can be measured with sensors associated with the output liquid blended fuel product 106. The steps representative of the calculation of RON and MON values and for the automated blending of the output liquid blended fuel product are shown in FIGS. 1, 2, and 3, wherein like steps are similarly labeled with like reference numbers.

Given a representative property that a blended fuel is targeted to achieve, within finite tolerances, there is a need to produce a liquid blended fuel that meets that target within the tolerances. For example, gasoline as a liquid blended fuel is often marketed at the gasoline pump at a service station as products each having a particular property, such as octane. For example, contemporary gasoline pumps often offer for sale gasoline having octanes of 87, 89, and 93. Some pumps alternately offer diesel fuel. The octane of the fuel at the pump is the Road Octane Number, which is the average between the research octane number (RON, as determined by ASTM D2699) and the motor octane number (MON, as determined by ASTM D2700) of the particular blended fuel. The RON and the MON of the fuel batch is typically certified in a lab prior to delivery to the particular tanks at the service station. From the certified RON and MON of the fuel, the Road Octane Number is determined by the equation:

$$\text{Road Octane Number} = \frac{RON + MON}{2} \qquad \text{Equ. (1)}$$

As discussed above, however, while the certified Road Octane Number may be determined as being within tolerances of, for example, 87, the actual RON value may be closer to 92 and the actual MON may be closer to 82. It is cheaper to produce a fuel at a RON closer to the targeted 87, and it is more efficient to not be burdened with having to wait for a subsequent delivery or blending with a fuel having RON and MON values closer to the targeted Road Octane Numbers for fuels to be sold and pumped into vehicles. If the RON and MON values of a blended fuel could be more accurately determined through timely calculations based on the actual properties of the component fuels, then the component fuels could be mixed differently to produce a fuel having RON and MON values closer to targets.

The RON and MON octane values of a liquid blended fuel product are a function of the octane values of each of the individual petroleum components that are blended together to produce the output blended fuel product and a function of the respective percentages of the various components being blended to produce the output blended fuel product. Contemporary techniques for calculating RON and MON values for a liquid blended fuel use a transformation method that relies on the RON and MON values of the blend components, the concentrations of the blend components, and the contents of the aromatics, olefins, and saturates of the blend components. While these techniques do a reasonably good job of predicting the Road Octane Number for the final blended fuel, the individual RON and MON predictions are poor. Based on data evaluated by the applicant, RON is typically over-predicted by an average of +0.6 and MON is under-predicted by an average of −0.7. A discussion and explanation of these techniques can be found in an article by Michael H. Rusin et al., entitled "A 'Transformation' Method for Calculating the Research and Motor Octane Numbers of Gasoline Blends," *Ind. Eng. Chem. Fundam.* 1981, 20, 195-204.

The original equations in use to calculate RON and MON values are extended in the present methods by expanding the saturates into their three components—normal paraffins (also referred to as n-paraffins), iso-paraffins (also referred to as i-paraffins), and naphthenes. Second order interaction terms are included to account for all interactions between these three saturate components along with the aromatics and olefins. The five measured properties of aromatics, olefins, normal paraffins, iso-paraffins, iso-paraffins, and naphthenes can be abbreviated as being the "PIANO" data for all component blends comprising the final liquid blended fuel.

Referring now to FIG. 2, the method begins at step 202 with the acquisition of data related to the aromatic, olefin, normal paraffin, iso-paraffin and naphthene properties of each of the plurality of petroleum products that are to be blended together as components to produce the final output liquid blended fuel product. At step 204, property transformation is applied against the acquired data for these five properties to obtain a transformed component property value for each of the plurality of petroleum components. This transformation is shown below according to Equations 2, with the following definitions:

Sensitivity S=RON−MON
Reference RON or Rref=90
Reference MON or Mref=90
(The value of 90 is chosen arbitrarily)
R=RON
M=MON
O=Olefins
A=Aromatics
N=Naphthenes
P=Normal Paraffins
I=Iso-Paraffins Hr and Hm represent the hydrocarbon type adjustments for RON and MON based on the second order interactions for the individual blend components HR and HM—same as above except for the blended fuel (with all blend components)

Tr and Tm are transformed RON and MON values for the individual blend components TR and TM—same as above except for the blended fuel (with all blend components)

$C_n$ and $K_p$ are constants derived from regression, with n being an integer value between and including 1 and 22; and with p being an integer value between and including 1 and 4. The components for performing the property transformation are calculated according to the following four equations, with the transformation property values being obtained according to equations 2e and 2f.

$$R(p)=R+C_1(R-Rref)*((R-M)/(1-C_1(R-Rref)+C_2(M-Mref)) \quad \text{Equ. (2a)}$$

$$M(p)=M+C_1(M-Mref)*((R-M)/(1-C_1(R-Rref)+C_2(M-Mref)) \quad \text{Equ. (2b)}$$

$$Hr=(C_3*O*I)(1+K_1*O)+(C_5*A*I)/(1+K_2*A)+ \\ (C_7*N*K_3*N)+(C_9*P*+K_4*P)+(C_{11}*O*A)+ \\ (C_{13}*O*P)+(C_{15}*O*N)+(C_{17}*A*N)+ \\ (C_{19}*A*P)+(C_{19}*A*P)+(C_{21}*N*P) \quad \text{Equ. (2c)}$$

$$Hm=(C_4*O*I)(1+K_1*O)+(C_6*A*I)/(1+K_2*A)+ \\ (C_8*N*K_3*N)+(C_{10}*P*+K_4*P)+(C_{12}*O*A)+ \\ (C_{14}*O*P)+(C_{16}*O*N)+(C_{18}*A*N)+ \\ (C_{20}*A*P)+(C_{22}*A*P)+(C_{21}*N*P) \quad \text{Equ. (2d)}$$

$$Tr=R(p)-Hr \quad \text{Equ. (2e)}$$

$$Tm=M(p)-Hm \quad \text{Equ. (2f)}$$

The transformed component property values Tr and Tm are linearly blended and weighted volumetrically at step 206 according to equations 3 to obtain a transformed blended property value for the blended fuel:

Calculate TR, TM, O, A, N, P and I as blended linearly and weighted volumetrically.

$$TR=\Sigma_{c=0}^n Tr^c V^c \quad \text{Equ. (3a)}$$

$$TM=\Sigma_{c=0}^n Tm^c V^c \quad \text{Equ. (3b)}$$

Calculate blended properties interactions HR and HM using same equations as 2c and 2d except that the P, I, A, N, O qualities to be used will be for the blended fuel (with all blend components).

A reverse property transformation is performed at step 208, according to equations 4, on the transformed blended property values for each of the components to obtain the predicted blended octane values for RON (R) and MON (M):

Adjust transformed octanes to include effects of hydrocarbon type interactions:

$$R(\text{prime})=TR+HR \quad \text{Equ. (4a)}$$

$$M(\text{prime})=TM+HM \quad \text{Equ. (4b)}$$

Calculate sensitivity at reference octane severity levels:

$$S=R(\text{prime})-M(\text{prime}) \quad \text{Equ. (4c)}$$

Adjust octanes from reference to actual severity levels.
The resulting R and M below are the blended octanes of the fuel.

$$R=R(\text{prime})-[C_1*S*(R(\text{prime})-Rref)/(1+C_1*S)] \quad \text{Equ. (4d)}$$

$$M=M(\text{prime})-[C_2*S*(M(\text{prime})-Mref)/(1+C_2*S)] \quad \text{Equ. (4e)}$$

At step 210, the percentage of each of the plurality of liquid blending components for combining to produce the liquid blended fuel is determined. Based on the predicted blended octane values and the determined percentages, the research octane number of the liquid blended fuel is calculated at step 212; and the motor octane number of the liquid blended fuel is calculated at step 214.

Figure 4:
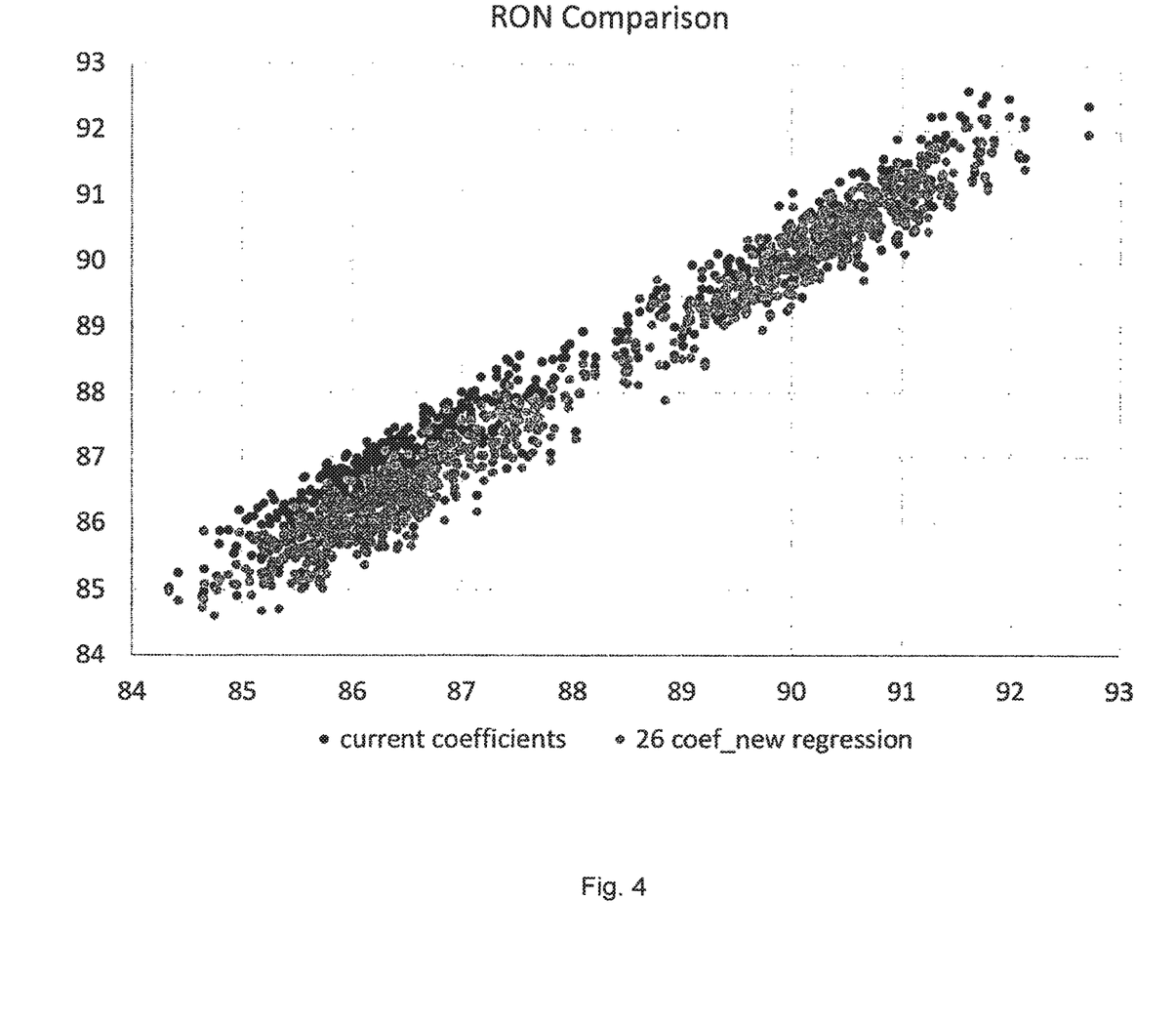
FIG. 4 is a chart showing the RON deviations between the calculated RON values under the disclosed methods versus the actual measured RON values.
Figure 5:
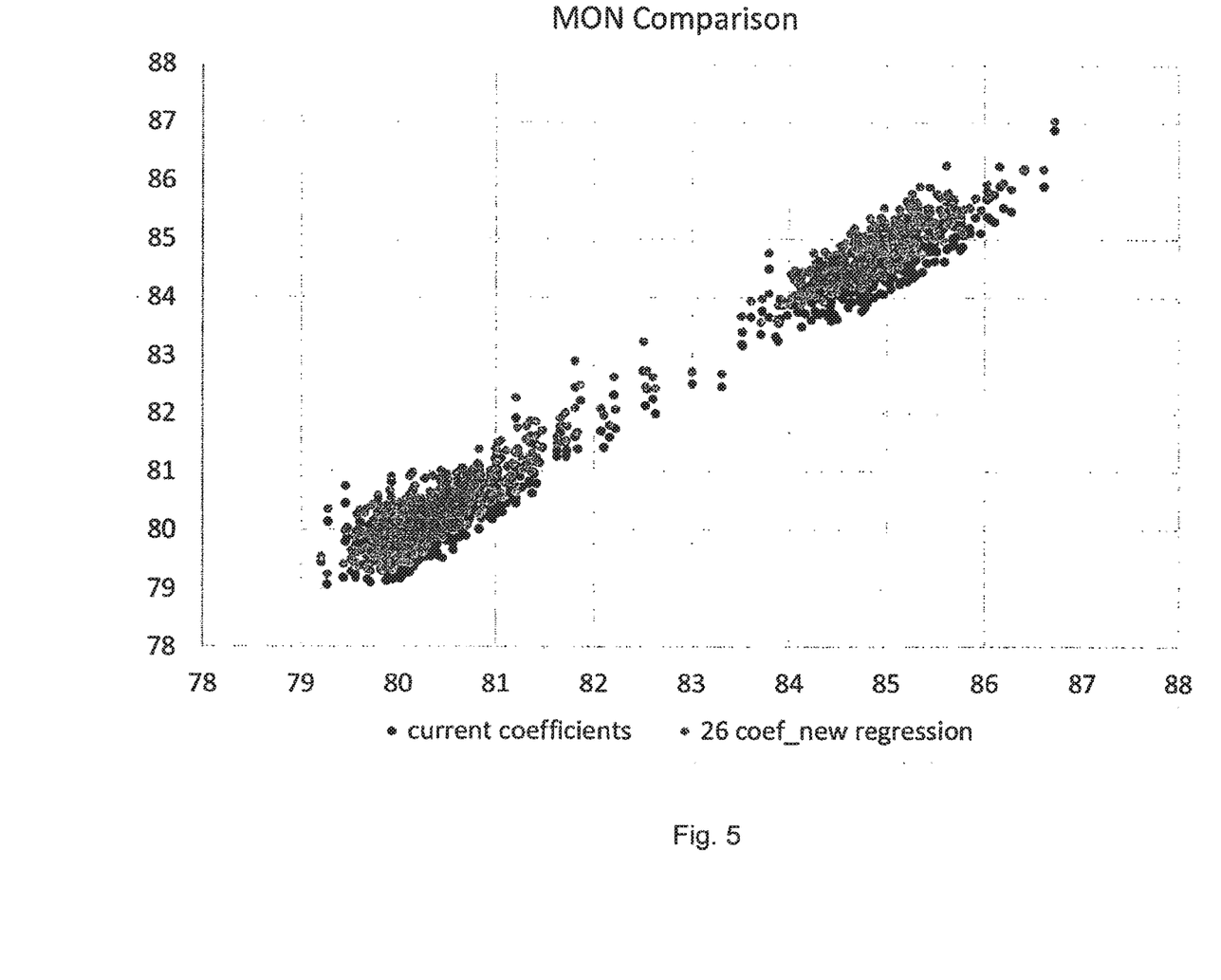
FIG. 5 is a chart showing the MON deviations between the calculated MON values under the disclosed methods versus the actual measured MON values.

Utilizing the above methods, coefficient values using nonlinear regression techniques were determined for over nine hundred fuel blends to compare the calculated RON and MON values against the actual measured RON and MON values for the fuel blends. Referring now to FIG. 4 and FIG. 5, there are respectively shown the difference coefficients between the calculated and measure values for RON and MON. Under prior techniques of calculating and predicting, the least squares error on the coefficient for RON values was approximately 0.32, and the least squares error on the coefficient for MON values was approximately 0.19. Under the methods disclosed herein, these difference coefficients were reduced by half or better to approximately 0.12 for the RON values and to approximately 0.10 for the MON values, thereby demonstrating the validity and the value of these new techniques.

Referring now to both FIGS. 1 and 3, there is shown a process and system for blending a plurality of liquid blending components to produce a liquid petroleum fuel with a targeted research octane number and a targeted motor octane number. At step 302, a targeted research octane number and a tolerance range for the research octane number is determined for the projected output liquid blended fuel product. Similarly, a targeted motor octane number and a tolerance range for the motor octane number for the output fuel product is determined at step 304. At step 202, data related to the aromatic, olefin, normal paraffin, iso-paraffin, and naphthene properties of each of a plurality of liquid blending components 102 is acquired. Typically, at this point in the process, the particular components 102 to be combined to produce the output liquid blended fuel product is known. However, it is within the scope of exemplary processes and systems to acquire property values for any number of possible components, with the understanding that the actual components to be blended together to produce the output liquid blended fuel will be determined at a point prior to the actual blending step.

At step 204, property transformation is applied against the acquired data for these five properties to obtain a transformed component property value for each of the plurality of petroleum components. This transformed component property value for each of the plurality of liquid blending components is linearly blended at step 206 to obtain a transformed blended property value for each of the plurality of liquid blended components. A reverse property transformation is performed on the transformed blended property value for each of the liquid blending components at step 208. At step 210, the percentages of each of the plurality of liquid blending components are determined, the combination of the blending components, when blended together according to the determined percentages, produces a blended fuel product comprising the determined targeted research octane number within the tolerance range for the research octane number and comprising the determined targeted motor octane number within the tolerance range for the motor octane number. Finally, at step 306, the determined percentage of each of the liquid blending components is utilized to tune a linear program model configured to produce the blended fuel product.

The description and illustration of one or more embodiments provided in this application are not intended to limit or restrict the scope of the invention as claimed. The embodiments, examples, and details provided in this application are considered sufficient to convey possession and to enable others to make and use the claimed invention. Having been provided with the description and illustration of the present application, one skill in the art may envision variations, modifications, and alternate embodiments falling within the spirit of the broader aspects of the claim invention and the general inventive concept embodied in this application that do not depart from the broader scope disclosed in this application.

What is claimed is:

1. A method for calculating the research octane number and the motor octane number for a liquid blended fuel, comprising:
    (a) acquiring data related to the aromatic, olefin, normal paraffin, iso-paraffin, and naphthene properties of each of a plurality of liquid blending components, wherein the plurality of liquid blending components are configured to be combined to produce a liquid blended fuel product;
    (b) transforming the acquired data for each of the plurality of liquid blending components to obtain a transformed component property value for each of the plurality of liquid blending components;
    (c) linearly blending the transformed component property value for each of the plurality of blending components to obtain a transformed blended property value for each of the plurality of liquid blending components;
    (d) performing reverse property transformation on the transformed blended property value for each of the plurality of liquid blending components;
    (e) determining the percentages of each of the plurality of liquid blending components for combining to produce the liquid blended fuel product;
    (f) calculating the research octane number of the blended fuel product;
    (g) calculating the motor octane number of the blended fuel product; and
    (h) utilizing the calculated research octane number and the calculated motor octane number to tune a linear program model for blending the liquid blending components into a blended fuel, the liquid blended fuel having a targeted road octane number within a road octane number tolerance.

2. The method according to claim 1, further comprising deriving a set of constants $C_n$ and $K_p$ from regression to be multiplied against the acquired data prior to transforming the acquired data, wherein n is an integer from one to twenty-two and p is an integer from one to four.

3. The method according to claim 1, further comprising:
    comparing the calculated research octane number for the blended fuel against a targeted research octane number;
    comparing the calculated motor octane number for the blended fuel against a targeted motor octane number;
    automatically issuing a notification if the calculated research octane number is not within a predetermined tolerance range of the targeted research octane number; and
    automatically issuing a notification if the calculated motor octane number is not within a predetermined tolerance range of the targeted motor octane number.

4. The method according to claim 3, further comprising:
    if a notification is issued based on the calculated research octane number not being within the predetermined research tolerance range, automatically modifying the blend proportions of the plurality of liquid blending components based on the calculated research octane number; and
    if a notification is issued based on the calculated motor octane number not being within the predetermined motor tolerance range, automatically modifying the blend proportions of the liquid blending components based on the calculated motor octane number.

5. The method according to claim 1, wherein the acquired data for each of the liquid blending components comprises:
    research octane number;
    motor octane number;
    proportions/concentration; and
    contents.

6. The method according to claim 1, wherein the blending of the liquid blending components is modified based on the tuned linear program model.

7. The method according to claim 1, wherein the percentage of one or more of the liquid blending components is automatically modified based on the tuned program model.

8. The method according to claim 1, wherein the road octane number of the blended fuel meets a targeted road octane number.

9. A method for blending a plurality of liquid blending components to produce a liquid petroleum fuel with a targeted research octane number and a targeted motor octane number, comprising:

(a) determining a targeted research octane number and a tolerance range for the research octane number;

(b) determining a targeted motor octane number and a tolerance range for the motor octane number;

(c) acquiring data related to the aromatic, olefin, normal paraffin, iso-paraffin, and naphthene properties of each of a plurality of liquid blending components;

(d) transforming the acquired data for each of the plurality of liquid blending components to obtain a transformed component property value for each of the plurality of liquid blending components;

(e) linearly blending the transformed component property value for each of the plurality of liquid blending components to obtain a transformed blended property value for each of the plurality of liquid blended components;

(f) performing reverse property transformation on the transformed blended property value for each of the liquid blending components;

(g) determining the percentage of each of the liquid blending components which, when blended together according to the determined percentages, produces a blended fuel product comprising the determined targeted research octane number within the tolerance range for the research octane number and comprising the determined targeted motor octane number within the tolerance range for the motor octane number; and (h) utilizing the determined percentage of each of the liquid blending components to tune a linear program model configured to produce the blended fuel product.

10. The method according to claim 9, wherein the linear program model directs a refinery to produce the blended fuel according to the determined proportions.

11. The method of claim 9, wherein the blended fuel is provided for certification by ASTM certified analysis.

12. The method of claim 11, wherein ASTM D2699 is used for certification of RON and ASTM D2700 is used for certification of MON.

13. The method of claim 11, wherein the blended fuel is certified, and then the blended fuel is transported to gasoline pumps.

* * * * *